(12) United States Patent
Fattman et al.

(10) Patent No.: US 6,326,524 B1
(45) Date of Patent: Dec. 4, 2001

(54) HYDROCOLLOID FOAM DRESSING

(75) Inventors: George F. Fattman, Mt. Laurel; Richard F. Bayless, Neshanic Station, both of NJ (US)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 09/517,490

(22) Filed: Mar. 2, 2000

Related U.S. Application Data

(60) Provisional application No. 60/122,364, filed on Mar. 2, 1999.

(51) Int. Cl.[7] .................................................. A61F 13/00
(52) U.S. Cl. .............................. 602/54; 602/41; 602/42; 602/43; 602/44; 602/45; 602/46
(58) Field of Search .................................. 602/41–47, 54

(56) References Cited

U.S. PATENT DOCUMENTS

| | | | |
|---|---|---|---|
| 3,797,494 | * | 3/1974 | Zaffaroni .......................... 424/434 |
| 4,292,972 | * | 10/1981 | Pawelchak et al. . |
| 4,775,374 | * | 10/1988 | Cilento et al. ..................... 604/344 |
| 5,429,591 | * | 7/1995 | Yamamoto et al. ................. 602/54 |

* cited by examiner

*Primary Examiner*—Michael A. Brown
*Assistant Examiner*—Lalita M. Hamilton
(74) *Attorney, Agent, or Firm*—Stuart E. Krieger

(57) ABSTRACT

The invention is a foamed, pressure sensitive, hydrocolloid adhesive for bonding to the body, and methods for its manufacture. The foamed structure of the adhesive itself improves absorbency, enables transmission of moisture through the adhesive, increases flexibility, and lowers product cost, all of which are key elements in making a product that is effective in adhering to the body.

25 Claims, 1 Drawing Sheet

HYDROCOLLOID FOAM DRESSING

This application claims benefit of provisional No. 60/122,364 filed Mar. 2, 1999.

BACKGROUND OF THE INVENTION

Adhesion to the body is a complicated process that is necessary to the functionality of a wide variety of products including but not limited to wound care dressings and ostomy appliances. It is known that adhesion to the skin for prolonged periods of time requires management of perspiration and other trans-epidermal water losses (TEWL). Pressure sensitive adhesives containing water-absorbing powders have been found effective in TEWL management. In particular, hydrocolloid adhesives are especially effective, and are preferred for this purpose.

It is common practice to manage wounds by covering them with a hydrocolloid wound dressing. These dressings typically consist of a pressure sensitive adhesive into which has been dispersed hydrocolloid particles. U.S. Pat. Nos. 3,339,546, 4,551,490, and others comprising the prior art of hydrocolloid containing pressure sensitive adhesives demonstrate this practice. Hydrocolloid wound dressings are exceptional in their ability to manage wound exudate. They achieve long wearing times, and provide a moist wound healing environment. This environment promotes autolytic debridement of the wound, non-traumatic dressing removal, and many other improvements over conventional adhesives and dressings that are believed to be beneficial to wound healing.

While hydrocolloid adhesives are known for the valuable characteristics described above, one limitation is their short-term rate of absorption. Typically the moisture absorbing capacity of a hydrocolloid adhesive is exceptional, and can exceed 5000 grams per square meter per day (gsm/d). However, absorption during the first hour is typically below 1000 gsm/d, and proportionally less at shorter times. As a result, hydrocolloid wound dressings are effective for a certain range of wounds, which produce light to moderate exudate. For heavily exudating wounds, the inability of hydrocolloid dressings to manage exudate leads to leakage of wound fluid sometime during the first 24 hours of wear.

For heavily exudating wounds, foamed polymers coated with a pressure sensitive adhesive on their wound contact surface are sometimes used. It is believed that their familiar design similar to strip bandages or gauze) and ability to absorb wound exudate relatively quickly are factors in their selection. However, these products suffer from several limitations. Unlike hydrocolloid wound dressings, these products are not noted for the preferred wound healing capabilities of hydrocolloid dressings. Further, they typically have limited long term absorbing capacity as their absorbency results primarily from a mechanical effect produced by the pores and cells of their foamed structure. Obviously, an additional limitation of conventional foamed dressings is that they will lose moisture when compressed. Finally, as the wound contact surface may be coated with a pressure sensitive adhesive to adhere to the body, the wound may be traumatized upon removal of the conventional foam dressing when that adhesive bonds to the healing wound itself.

As an ostomy device, a foamed hydrocolloid adhesive skin barrier offers several benefits over the state of the art. Flexibility of the skin barrier is greatly enhanced compared with a non-foamed barrier of the same composition. A secure attachment to the skin can be achieved, while reducing the removal force by virtue of the lessened contact area. As for wound dressings, intimate contact between hydrocolloid adhesives and the skin of an ostomate is well established as a beneficial attribute. Finally, the ability of the foamed structure to conform to irregular surfaces of the body to which an ostomy device must be attached is improvement over non-foamed adhesives.

SUMMARY OF THE INVENTION

The invention described herein improves the state of the art for hydrocolloid adhesives by changing the structure of the adhesive itself. Gas bubbles introduced into the pressure sensitive adhesive during the manufacturing process create a lightweight, cellular, two-phase structure. Properties of the foamed material depend on the individual properties of both the gas and solid phases. The size and extent of each phase are key characteristics in describing the structure of the foamed adhesive. In particular, the size and shape of cells in the gas phase determine the ultimate properties of a foamed structure for a given solid phase. Additionally, the density of the overall foamed structure can be useful for characterization. The structure of the foam may be open celled, with two or more cells connected by tunnels, or closed celled, where cells are predominantly isolated from one another.

Foaming hydrocolloid adhesives increases their flexibility and lowers the density and cost of the overall adhesive product. Creation of the foamed structure also results in an increase in surface area of the adhesive exposed to the contact surface. The increased surface area is particularly useful for adhesion to the body as it enables rapid absorption of liquids by a mechanical means. The time scale for absorbing liquids by physically trapping them in the cells of the foamed adhesive is significantly shorter than that for absorbing liquids chemically by the forces of attraction in the hydrocolloids themselves. Further, when liquids are trapped in the cells of the foam, the area of contact between the absorbed liquid and the solid phase of the adhesive is increased. As a result, a second, chemical based absorption process begins. These two processes work together to increase the overall absorption rate for a foamed hydrocolloid adhesive.

Depending on the size, shape, and extent of the cells, the foaming process can create a structure where a tortuous path of open cells and tunnels connects two exterior surfaces of a foam. In that case, moisture from one surface can rapidly be conducted to another surface. In the case of a wound dressing, this process can significantly enhance the overall rate and capacity for management of TEWL. Wound fluid quickly fills the cells of the foamed adhesive and is then conducted to another surface of the adhesive. If that surface is exposed to the atmosphere, the fluid can evaporate. If that surface is laminated with a film capable of transmitting moisture or moisture vapor, then wound exudate can pass through that film. In either case, fluid is managed at a faster rate and to a greater extent (capacity) than is possible using unfoamed hydrocolloid dressings. Extension of the concept of a foamed hydrocolloid adhesive to other kinds of body adhesion is clear to those skilled in the art. For example, improvements resulting from the foamed structure enable the adhesive to manage a greater quantity of perspiration generated at a faster rate than an unfoamed product. This improvement is useful in general for adhesion to the body, and in particular for wound dressings and ostomy appliances as cited above.

DETAILED EMBODIMENT OF THE INVENTION

Figure 1:
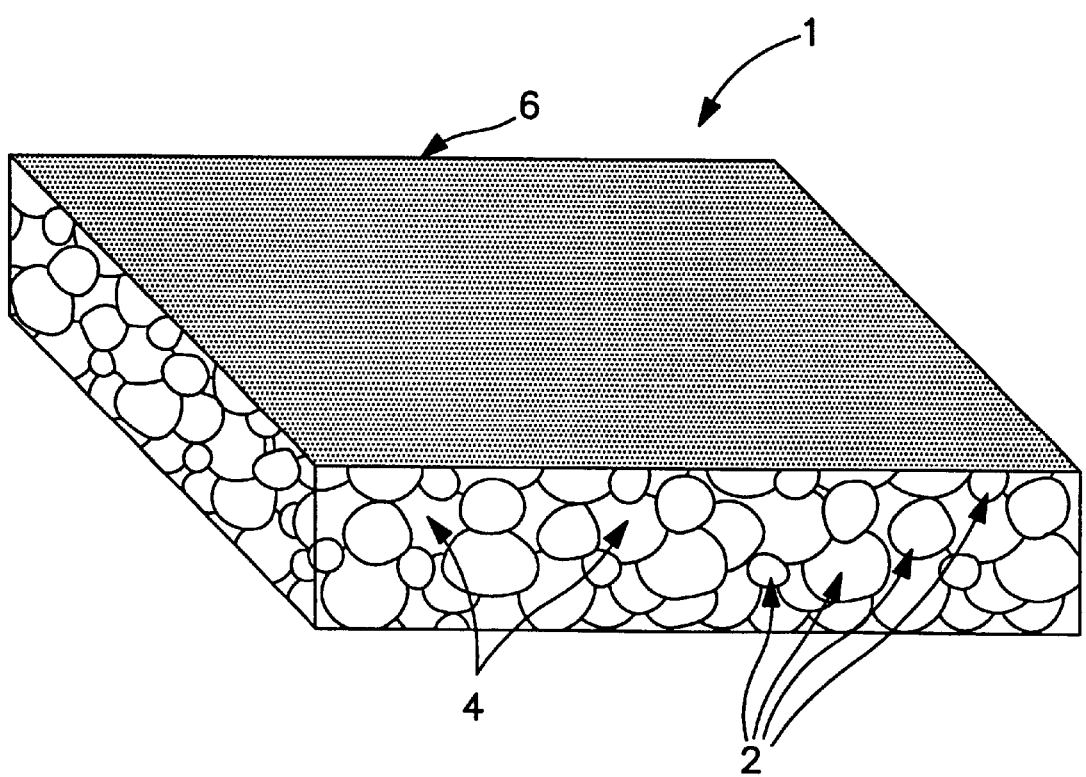
FIG. 1 is a perspective view of a hydrocolloid foam dressing pursuant to the present invention.

In FIG. 1, a hydrocolloid foam dressing 1 according to the present invention is shown with gas bubbles 2 distributed throughout hydrocolloid adhesive 4. The dressing 1 includes a cover layer 6.

Foamed hydrocolloid adhesives can be achieved by introducing gas bubbles into the pressure sensitive hydrocolloid adhesive. There are two preferred methods for accomplishing this introduction. First, chemical blowing agents or other materials added to the adhesive formula itself may generate gas bubbles by a variety of mechanisms. These mechanisms include but are not limited to chemical reaction, physical changes (for example, the breaking of microspherical particles containing the gas), thermal decomposition or chemical degradation, leaching of a dispersed phase, volatilization of low boiling materials, by expansion of gas filled materials such as beads or other gas containers, or by a combination of these methods.

In the second preferred method for creating a foamed hydrocolloid adhesive a mechanical process can be used to add a physical blowing agent, similar to whipping the solid phase into a froth, thus creating a foamed structure. Many processes are possible including incorporation of air, nitrogen, carbon dioxide, or other gases or low boiling point volatile liquids during the compounding, extrusion or converting processes of manufacturing the adhesive.

Any of the commercially known chemical blowing agents may be used, but the preferred agents will have activation temperatures below about 160° C., preferably with peak gas generation occurring within the range of about 100° C. to about 135° C. The chemical blowing agents must also be non-toxic, skin friendly, and environmentally safe, both before and after decomposition.

The term chemical blowing agent is used herein to cover the use of single or multiple component chemicals in a mixture or paste. Suitable chemical blowing agents include the carbonates of alkali metals, such as ammonium carbonate, ammonium bicarbonate, sodium carbonate, sodium bicarbonate, and calcium carbonate. Improved gas generation can be obtained by making a mixture of carbonates of alkali metals and various organic acids including, but not limited to, stearic, oleic, phthalic, maleic, citric, tartaric acid, and abietic acids. An excess of organic acids are preferably added to the carbonates of alkali metals, so the final reaction products have an acidic character.

The amount of chemical blowing agent to be added to hydrocolloid adhesive can range from about 0.01% up to about 90% by weight, with a practical range including about 1% up to about 20%. The amount to be added can be determined by measuring the amount of gas generated from a candidate mixture and calculating the amount of foaming required of the final product, tempered by experience of the amount of gas lost to atmosphere during the foaming process.

One embodiment of a chemical blowing agent is a mixture of sodium bicarbonate and citric acid. The stoichiometric ratio for these two components should be 3 moles of sodium bicarbonate to 1 mole of citric acid. To provide an excess of acid to base, the molar ratio of sodium bicarbonate to citric acid can range from 3 to 1 up to 1 to 3 or higher, preferably near 2 to 1.

The adhesive mass containing the chemical blowing agent can be processed into a foam under any of the techniques described above under the first preferred method. Processing includes forming the adhesive mass into sheet, either flat or contoured, by extrusion or by pressing or by injection molding or by thermoforming or by any other typical adhesive processing method. The adhesive sheet will be laminated to suitable films and release carriers and then heated sufficiently to cause the decomposition of the chemical blowing agent, thereby creating a foamed hydrocolloid adhesive. Cutting of the adhesive sheet into a wound dressing or an ostomy wafer or any other typical hydrocolloid adhesive product shape can be performed either before or after the foaming of the adhesive mass. Alternatively, the adhesive mass can be foamed during the extrusion process, followed by calendaring, lamination, and cutting of the foamed sheet into a product.

EXAMPLE

For one example of how a foamed hydrocolloid adhesive may be created, one adhesive formula listed in U.S. Pat. No. 4,551,490 was blended with a chemical blowing agent, shaped into a product, and foamed by addition of heat.

The base hydrocolloid adhesive formulation used is substantially as described in U.S. Pat. No. 4,551,490 under Example 4. The base hydrocolloid adhesive formulation was manufactured using the adhesive mixing process described in U.S. Pat. No. 4,551,490 under Example 1. The precise adhesive formulation and process used follows.

The mineral oil, polyisobutylene, SIS rubber, and Antioxidant are combined in a sigma blade mixer with heating (about 115° C.) and agitating for approximately 1.0 to 2.5 hours. The mixture is cooled to about 100° C. and after another 30 minutes of blending, the sodium carboxymethylcellulose, cross-inked sodium carboxymethylcellulose and Tackifier are added. Mixing is continued at about 100° C. for 30 minutes until a homogeneous mass is obtained. The homogeneous mass is removed from the mixer and is allowed to cool. The ethylene propylene rubber is then added to the mixer and masticated at 115° C. for 10 minutes. The cooled homogeneous mass is then added into the mixer along with the masticated ethylene propylene rubber and allowed to mix for 30 minutes at 115° C. or until the entire hydrocolloid adhesive mixture is homogeneous.

| Percentage | Ingredient |
| --- | --- |
| 8.1% | Polyisobutylene, low molecular weight, medium hard |
| 21.8% | Sodium carboxymethylcellulose |
| 8.0% | Cross-linked sodium Carboxymethylcellulose |
| 17.4% | Mineral Oil |
| 17.5% | Styrene-Isoprene-Styrene copolymer rubber |
| 10.9% | Tackifier, pentaerythritol ester of rosin |
| 1.3% | Antioxidant |
| 15.0% | Ethylene Propylene Rubber |

The fully formulated base hydrocolloid adhesive was then heated and masticated in a sigma blade mixer at 80° C. for five minutes, in preparation for the addition of the chemical blowing agent. The chemical blowing agent used is the combination of sodium bicarbonate and citric acid at a molar ratio of 2 to 1, added at the 6% by weight level. The chemical blowing agent was then added to the heated and masticated adhesive mass and mixed for twenty minutes until fully dispersed and distributed in the adhesive mass. The adhesive mass with the incorporated chemical blowing agent was then removed from the sigma blade mixer and allowed to cool.

The prepared adhesive mass was then characterized using a Haake Rheocord equipped with a gas flow meter suitable for measuring chemical blowing agent gas generation over a range of temperatures. Using a temperature sweep with a rate of rise of 1.4° C. per minute, gas generation began at 113° C., had a first peak at 124° C. and had a second peak at 160° C.

The prepared adhesive mass was then formed into a sheet using a press set at 80° C., laminated to the desired carrier substrates, and cut into a product shape, in this case a 4" by 4" dressing. Multiple samples of the dressing were then placed into an oven set at various temperatures, for ten minutes each, which activated the decomposition of the chemical blowing agent, thereby creating a foamed hydrocolloid adhesive product.

The foamed product density varied depending on the foaming temperature. Dressings foamed at the higher temperatures had lower densities and larger cell sizes.

| Sample Treatment | Density, g/cc |
| --- | --- |
| Not foamed | 1.00 |
| 135° C. | 0.85 |
| 150° C. | 0.58 |
| 160° C. | 0.45 |

Measurements, all in millimeters diameter, of the cell size distributions for the dressings foamed at various temperatures were as follows:

| Temperature | Smallest cell | Typical cell | Maximum cell | Notes |
| --- | --- | --- | --- | --- |
| 125° C. | 0.02 | 0.5 | 1.0 | Closed cells, mostly isolated |
| 135° C. | 0.2 | 0.6 | 2.0 | Some open cells, connected |
| 150° C. | 0.2 | 1.6 | 4.0 | Open cells, well connected |

Fluid uptake measurements were performed on unfoamed samples and on samples foamed at 150° C. The fluid uptake measurements used 0.9% aqueous saline as the fluid and were held in a conditioning unit at 38° C., to simulate physiological conditions. Fluid uptake, in grams per square meter, was measured at three different time intervals.

| | Average Fluid uptake at each Time interval, g/m^2 | | |
| --- | --- | --- | --- |
| Condition | 1 hour | 2 hour | 18.5 hours |
| Not Foamed | 179 | 247 | 687 |
| Foamed | 497 | 787 | 1319 |
| Ratio of Uptakes | 2.8 times | 3.2 times | 1.9 times |

As can be seen from the large increase in the uptake of the foamed adhesive compared to the unfoamed adhesive, the effect of foaming the hydrocolloid adhesive will provide improvements in transferring and absorbing moisture, perspiration, and wound fluid. The application of this technology to hydrocolloid adhesives will provide improvement of the performance of the total wound dressing or ostomy appliance.

For some wounds, it may be desirable to have a dressing that includes a foamed adhesive laminated with a moisture retaining material. This moisture retaining material may include a fibrous or non-fibrous, woven or non-woven, or foamed or non-foamed stock material, or another material possessing capillaries, cells, pores or other channels or compartments for the purpose of retaining or absorbing moisture. This lamination material may be combined with a moisture retention aid including hydrocolloids, super absorbents, or other liquid gelling, liquid absorbing, or liquid retaining components for retaining or controlling liquid and moisture It may also be desirable to laminate the foamed adhesive with an occlusive layer for the purpose of retaining moisture or managing transmission.

We claim:

1. A process for manufacturing an adhesive dressing, the steps comprising:

forming a mass of pressure-sensitive hydrocolloid adhesive, introducing gas generating material into the mass of hydrocolloid adhesive;

shaping the mass of hydrocolloid adhesive into a predetermined shape for application to skin as a dressing; and generating gas bubbles in the adhesive by activating the gas generating material, wherein said gas bubbles are distributed through said predeterminedly shaped adhesive as cells having a diameter in the range of 0.2 to 4.0 millimeters.

2. The process of claim 1 wherein the gas generating material includes a chemical blowing agent.

3. The process of claim 2 wherein the chemical blowing agent includes a carbonate.

4. The process of claim 2 wherein the chemical blowing agent includes a mixture of sodium bicarbonate and citric acid.

5. The process of claim 2 wherein the chemical blowing agent has a range of approximately 1% to 20% by weight.

6. The process of claim 3 wherein the carbonate is one or more compounds selected from ammonium carbonate, ammonium bicarbonate, sodium carbonate, sodium bicarbonate and calcium carbonate.

7. The process of claim 1 wherein the gas generating material includes an acid.

8. The process of claim 7 wherein the acid is one or more compounds selected from stearic, oleic, phthalic, maleic, citric, tartaric and abietic acids.

9. The process of claim 1 wherein the step of shaping includes making said adhesive into a sheet.

10. The process of claim 1 further comprising the step of laminating at least one layer onto said predetermined shape.

11. The process of claim 1 further comprising the step of laminating a non-occlusive or occlusive layer onto said predetermined shape.

12. The process of claim 1 wherein the step of generating gas bubbles includes incorporating a chemical blowing agent into the hydrocolloid adhesive and heating the blowing agent.

13. The process of claim 1 wherein, the gas bubbles includes air, nitrogen or carbon dioxide.

14. A process for manufacturing an adhesive dressing, the steps comprising:

forming a mass of a pressure-sensitive hydrocolloid adhesive;

introducing gas bubbles into the mass of hydrocolloid adhesive, wherein said gas bubbles are distributed through said predeterminedly shaped adhesive as cells having a diameter in the range of 0.2 to 4.0 millimeters; and forming the adhesive into a predetermined shape for application to skin as a dressing.

15. The process of claim 14 where the step of introducing includes mechanically introducing.

16. The process of claim 14 where the step of mechanically introducing includes whipping the mass into a froth.

17. A dressing for absorbing exudate from a wound comprising a pressure-sensitive hydrocolloid adhesive, said hydrocolloid adhesive including gas bubbles predeterminedly incorporated therein, said hydrocolloid adhesive being shaped for application to skin as a dressing, wherein said gas bubbles are distributed through said predeterminedly shaped adhesive as cells having a diameter in the range of 0.2 to 4.0 millimeters.

18. The dressing of claim 17 wherein said gas bubbles are air, nitrogen or carbon dioxide.

19. The dressing of claim 17 wherein said hydrocolloid adhesive with gas bubbles incorporated is 45 to 85% of the density of the hydrocolloid adhesive without gas bubble predeterminedly incorporated therein.

20. The dressing of claim 17 wherein said hydrocolloid adhesive with gas bubbles predeterminedly incorporated therein uptakes 0.9% aqueous saline at 38° C. in grams per square meter in one hour at more than 2 times the hydrocolloid adhesive without gas bubbles predeterminedly incorporated therein.

21. The dressing of claim 17 incorporated into a wound dressing.

22. The dressing of claim 17 incorporated into an ostomy device.

23. A dressing for absorbing exudate from a wound comprising a pressure-sensitive hydrocolloid adhesive, said hydrocolloid adhesive including gas bubbles predeterminedly incorporated therein, said hydrocolloid adhesive being shaped for application to skin as a dressing, wherein said hydrocolloid adhesive uptakes 0.9% aqueous saline at 38° C. in grams per square meter in one hour at more than 2 times the hydrocolloid adhesive without gas bubbles predeterminedly incorporated therein.

24. A process for manufacturing an adhesive dressing, the steps comprising:

forming a mass of pressure-sensitive hydrocolloid adhesive;

forming the adhesive into a predetermined shape for application to skin as a dressing; and introducing gas bubbles into said predeterminedly shaped adhesive so as to form therein cells having a diameter in a range of 0.2 to 4.0 millimeters.

25. A process for manufacturing an adhesive dressing, the steps comprising:

forming a mass of pressure-sensitive hydrocolloid adhesive;

introducing gas bubbles into the mass of hydrocolloid adhesive; and forming the hydrocolloid into a predetermined shape wherein said hydrocolloid adhesive uptakes 0.9% aqueous saline at 38° C. in grams per square meter in one hour at more than 2 times the hydrocolloid adhesive without gas bubbles introduced therein.

* * * * *